(12) United States Patent
Garabedian et al.

(10) Patent No.: US 6,995,243 B2
(45) Date of Patent: Feb. 7, 2006

(54) ANTIBODIES THAT RECOGNIZE AND BIND PHOSPHORYLATED HUMAN GLUCOCORTICOID RECEPTOR AND METHODS OF USING SAME

(75) Inventors: Michael Garabedian, New York, NY (US); Zhen Wang, New York, NY (US)

(73) Assignee: New York University, New York, NY (US)

( * ) Notice: Subject to any disclaimer, the term of this patent is extended or adjusted under 35 U.S.C. 154(b) by 40 days.

(21) Appl. No.: 10/629,913

(22) Filed: Jul. 30, 2003

(65) Prior Publication Data

US 2004/0248210 A1 Dec. 9, 2004

Related U.S. Application Data

(60) Provisional application No. 60/402,706, filed on Aug. 13, 2002.

(51) Int. Cl.
| | |
|---|---|
| C07K 16/00 | (2006.01) |
| C07K 16/18 | (2006.01) |
| C07K 16/28 | (2006.01) |
| G01N 33/53 | (2006.01) |
| G01N 33/68 | (2006.01) |

(52) U.S. Cl. .............. 530/387.9; 530/388.1; 530/389.1; 435/7.21; 424/130.1
(58) Field of Classification Search ............ 530/387.1, 530/387.9, 388.22, 388.1, 389.1; 435/7.21; 424/130.1
See application file for complete search history.

(56) References Cited

OTHER PUBLICATIONS

Wang et al., J. Biol. Chem., vol. 277, Issue 29, 26573-26580, Jul. 19, 2002.*

* cited by examiner

*Primary Examiner*—Robert C. Hayes
*Assistant Examiner*—Daniel C Gamett
(74) *Attorney, Agent, or Firm*—Browdy and Neimark, PLLC

(57) ABSTRACT

A molecule containing the antigen binding portion of an antibody specific for human glucocorticoid receptor phosphorylated at residue Ser211, Ser226 or Ser203 is obtained and a method of determining the presence of activated glucocorticoid receptors in cells from human glucocorticoid responsive tissue and a method of screening for a glucocorticoid agonist using the molecule, which is preferably an antibody, are provided in the present invention.

12 Claims, 9 Drawing Sheets

Immunoblot

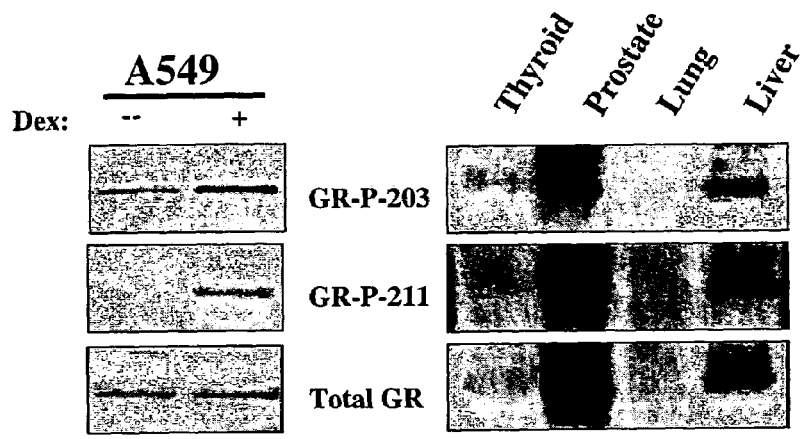
FIG. 3
FIG. 4
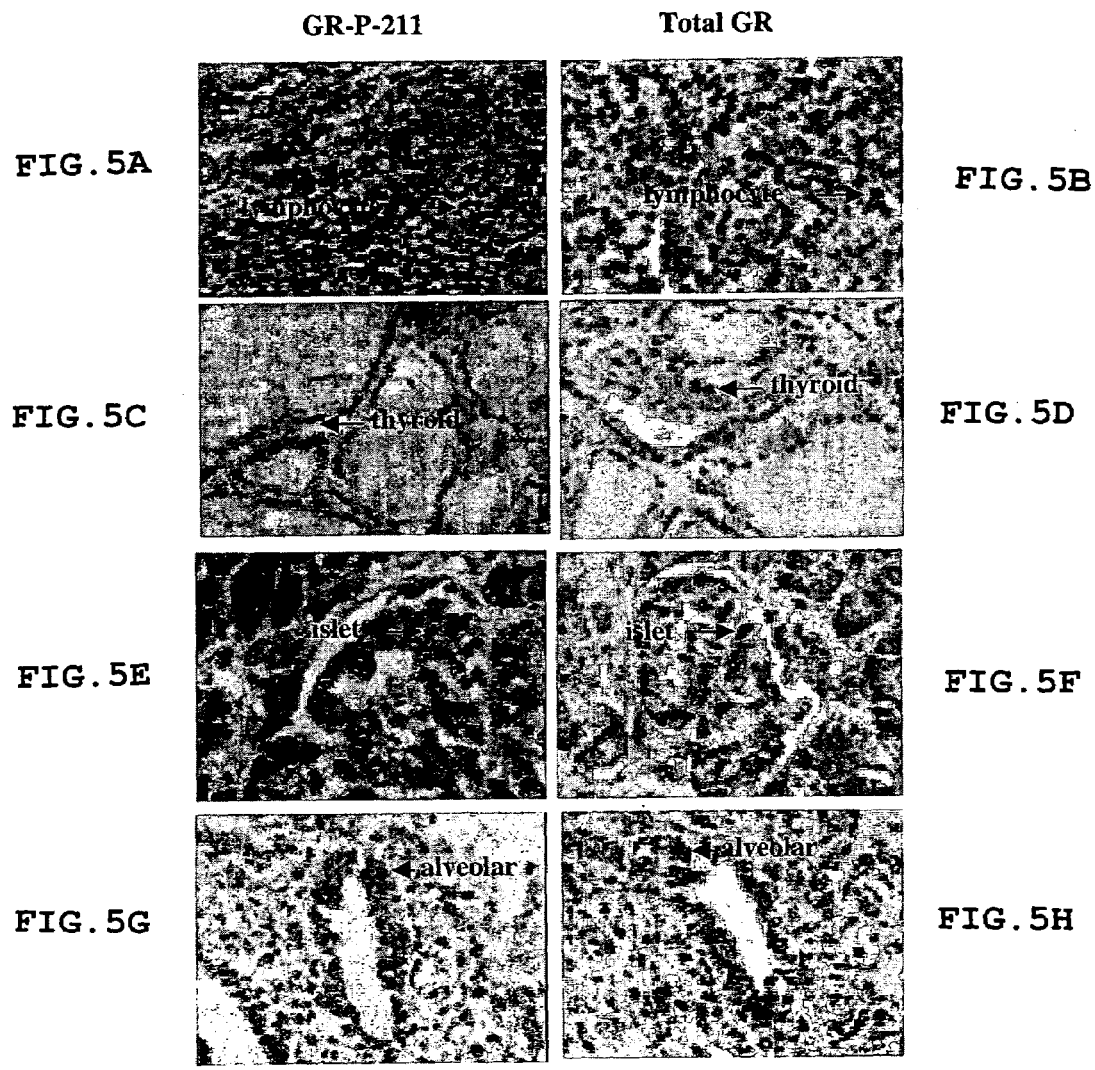
FIG. 5A FIG. 5B
FIG. 5C FIG. 5D
FIG. 5E FIG. 5F
FIG. 5G FIG. 5H

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Residue 10 is phosphorylated.

<400> SEQUENCE: 1

Leu Gln Asp Leu Glu Phe Ser Ser Gly Ser Pro Gly Lys Glu
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Residue 10 is phosphorylated.

<400> SEQUENCE: 2

Gly Ser Pro Gly Lys Glu Thr Asn Glu Ser Pro Trp Arg Ser
1               5                   10

<210> SEQ ID NO 3
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (9)..(9)
<223> OTHER INFORMATION: residue 9 is phosphorylated

<400> SEQUENCE: 3

Leu Leu Ile Asp Glu Asn Leu Leu Ser Pro Leu Ala Gly
```

<210> SEQ ID NO 4
<211> LENGTH: 777
<212> TYPE: PRT
<213> ORGANISM: Homo sapiens

<400> SEQUENCE: 4

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365
```

```
Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
770                 775
```

ANTIBODIES THAT RECOGNIZE AND BIND PHOSPHORYLATED HUMAN GLUCOCORTICOID RECEPTOR AND METHODS OF USING SAME

CROSS REFERENCE TO RELATED APPLICATIONS

This application claims priority under 35 U.S.C. §119(e) from U.S. provisional application No. 60/402,706 filed Aug. 13, 2002, the entire content of which is hereby incorporated by reference.

GOVERNMENT LICENSE RIGHTS

The experiments performed in this application were supported in part by the National Institutes of Health, Grant No. R01 DK54836. The U.S. Government has a paid-up license in this invention and the right in limited circumstances to require the patent owner to license others on reasonable terms as provided for by the terms of Grant No. R01 DK54836 awarded by the National Institutes of Health.

BACKGROUND OF THE INVENTION

1. Field of the Invention

The present invention relates to antibodies specific for epitopes of human glucocorticoid receptor in which a serine residue is phosphorylated. The present invention also relates to a method for determining the presence of activated glucocorticoid receptors and to a method for screening a glucocorticoid agonist.

2. Description of the Related Art

The glucocorticoid receptor (GR) is a phosphoprotein that regulates a wide range of metabolic and developmental processes by controlling the expression of target genes in a hormone-dependent and cell-specific manner (Reichardt et al., 2000 and Yamamoto et al., 1985). GR is structurally similar to other members of the nuclear receptor superfamily, in that separate receptor activities such as DNA and ligand binding are localized to distinct regions of the protein (Weinberger et al., 1985 and Hollenberg et al., 1985). GR contains a constitutive activation function, AF-1, in the N-terminus, and a ligand-dependent AF-2 at the C-terminus (Godowski et al., 1987). In absence of ligand, the hsp90-based chaperone complex represses GR regulatory activities (Pratt et al., 1997). Hormone binding relieves this repression and results in a conformational change in the receptor, which, in turn, promotes GR DNA binding, association with additional transcriptional regulatory cofactors and regulation of target genes (Jenkins et al., 2001).

Although ligand binding is essential for the activation of GR, the receptor is also subject to post-translational modification through phosphorylation (Bodwell et al., 1998). GR is phosphorylated in the absence of hormone, with additional phosphorylation occurring in conjunction with agonist, but not antagonist binding. Orti et al. showed that GR is hyperphosphorylated after it has become activated and acquires the ability to bind to DNA (Orti et al., 1993). It has been suggested that hormone-dependent phosphorylation of GR may determine target promoter specificity, cofactor interaction, strength and duration of receptor signaling, and receptor stability (Garabedian et al., 1998).

Bodwell et al. have identified seven phosphorylation sites in the mouse GR (mGR) over-expressed in Chinese hamster ovary cells by direct sequencing of phosphorylated peptides (Bodwell et al., 1991). All seven phosphorylated residues are clustered in the N-terminal region of the receptor. Through peptide mapping and mutagenesis studies, the laboratory of the present inventors has identified four predominant sites of phosphorylation on rat GR (rGR) expressed in mammalian cells and in yeast, that coincide with a subset of sites identified in mGR (Pocuca et al., 1998 and Krstic et al., 1997). Among them, two sites S224 and S232 corresponding to S203 and S211 in human GR were phosphorylated to a greater extent in the presence of hormone. The laboratory of the present inventors has also identified the cyclin-dependent kinases (Cdks) as potential kinases that modify S224 and S232 in vitro. Mutations in the Cdk catalytic subunit, $p34^{CDC28}$ or regulatory cyclin subunits reduced receptor-dependent transcriptional activation in a reconstituted GR signaling system in yeast, indicating that Cdk function is necessary for full receptor-mediated transcriptional enhancement (Krstic et al., 1997).

Previous studies by Mason and Housley suggest that single or multiple phosphorylation site mutations in mouse GR (mGR) had little effect on receptor transcriptional activation, subcellular localization or activity in response to cAMP treatment (Mason et al., 1993). Similar results were obtained by Almlof et al. when phosphorylation site mutants in human GR where analyzed in yeast (Almlof et al., 1995). Webster et al. reported that single or multiple phosphorylation site mutations had little effect on mGR expression, nuclear translocation and transcriptional activation from a complex MMTV promoter (Webster et al., 1997). Importantly, they also showed that the phosphorylation status of mGR had a substantial effect on transcriptional activation from a GR-responsive reporter containing a minimal E1b-promoter, suggesting that the effect of GR phosphorylation on transcriptional activation appears promoter-specific. However, the mechanism by which phosphorylation affects GR transcriptional regulation remains enigmatic.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a molecule comprising the antigen binding portion of an antibody specific for human glucocorticoid receptor (GR) phosphorylated at residue Ser211, Ser226 or Ser203, which molecule is preferably an antibody.

The present invention also provides a method for determining the presence of activated glucocorticoid receptors in cells obtained from human glucocorticoid responsive tissue, where detection of binding of a molecule comprising the antigen binding portion of an antibody specific for human GR phosphorylated at residue Ser211 or Ser226 to cells treated with glucocorticoid, or to extracts of such treated cells, provides a determination of the presence of activated human GR in cells from glucocorticoid responsive tissue of an individual.

The present invention further provides a method of screening for a glucocorticoid agonist by testing potential glucocorticoid agonists for the ability to activate human glucocorticoid receptor, where activation is determined by detecting binding of a molecule comprising the antigen binding portion of an antibody specific for human GR phosphorylated at residue Ser211 or Ser226 to cells treated with a potential glucocorticoid agonist, or to an extract of such treated cells.

BRIEF DESCRIPTION OF THE DRAWINGS

FIGS. 1A–1C show schematically the structure of human glucocorticoid receptor (hGR) functional domains and phosphorylated residues of the hGR. FIG. 1A is a schematic representation of hGR with phosphorylation sites corresponding to those in mGR as determined by Bodwell et al. (Burnstein et al., 1994). The sequences of the hGR phosphopeptides (SEQ ID NOs:1 and 2) used to produce the antibodies are shown in FIGS. 1B and 1C.

In FIG. 2A, whole cell extracts prepared from U2OS cells expressing an HA-tagged hGR (U2OS-hGR), either wild type or phosphorylation site mutant derivatives S203A or S211A, untreated or treated with 100 nM Dex for 1 h were analyzed by immunoblotting with phospho-S203 (top panel), phospho-S211 (center panel) or HA antibodies (bottom panel) as a measure of total GR. In FIG. 2B, whole cell extracts prepared from U2OS cells expressing an HA-tagged hGR (U2OS-hGR) with 100 nm Dex for 1 h and analyzed by immunoblotting with phospho-S226 (top panel) or HA antibodies as measure of total GR (bottom panel). In FIG. 2C, whole cell extracts prepared from U2OS cells expressing either the wild type or phosphorylation site mutant derivative S225A, untreated or treated with 100 nM Dex for 1 h and analyzed by immunoblotting with phospho-S226 antibody.

FIG. 3 show immunoblots of whole cell extracts prepared from A549 cells expressing endogenous hGR which were untreated (−) or treated with 100 nM Dex for 1 h and then analyzed by immunoblotting with phospho-S203 (top), phospho-S211 (center) or the phosphorylation state-independent antibody, GR N499 (bottom) as a measure of total GR.

FIG. 4 is an immunoblot showing expression of endogenous phospho-GR in human tissues. Extracts from human tissues (50 $\mu$g/lane, Protein Medleys, Clontech) were analyzed by immunoblotting with phospho-S203 (top), phospho-S211 (center) or the phosphorylation state-independent antibody, GR N499 (bottom).

FIGS. 5A–5H are immunohistochemical analyses showing expression of endogenous GR phospho-S211 in human tissues. The gallery of images (400×) shows immunohistochemical analysis of paraffin-embedded human tissues treated with the GR phospho-S211 antibody (FIGS. 5A, 5C, 5E, and 5G) or a GR antibody that recognizes GR in a phosphorylation-state independent manner (total GR) (FIGS. 5B, 5D, 5F, and 5H). GR phospho-S211 reactivity is observed within the nuclei of human lymphocytes (FIG. 5A), thyroid cells (FIG. 5C), islet cells of the pancreas (FIG. 5E), but not in the alveolar cells of the lung (FIG. 5G), despite the presence of GR in all tissues examined (FIGS. 5B, 5D, 5F and 5H). No staining above background is observed when preimmune serum is used (not shown).

In FIG. 6A, U2OS-hGR were treated with ethanol (−) or the ligands indicated (100 nM) for 1 hour and whole cell extracts were prepared. For antagonism experiments, a 10-fold excess of RU486 (1 $\mu$M) or ZK299 (1 $\mu$M) were added simultaneously with 100 nM Dex for 1 h prior to cell lysis. Equal amounts of protein from each treatment were analyzed by immunoblotting with either phospho-S203, phospho-S211 or HA antibodies, reflective of the amount of total GR present in each lane. In FIG. 6B, U2OS-hGR cells were transiently transfected with the MMTV-luciferase reporter construct along with pCMV-lacZ as an internal control. After 16 h, the cells were treated with ligands indicated (100 nM) for 1 h, conditions identical to those used for the immunoblot analysis, and luciferase activity determined.

In FIG. 7C, quantitative analysis of immunoblot results in panel B normalized to total GR detected by HA. The data shown are from a single experiment that is representative of at least three independent experiments.

DETAILED DESCRIPTION OF THE INVENTION

Figure 1A:
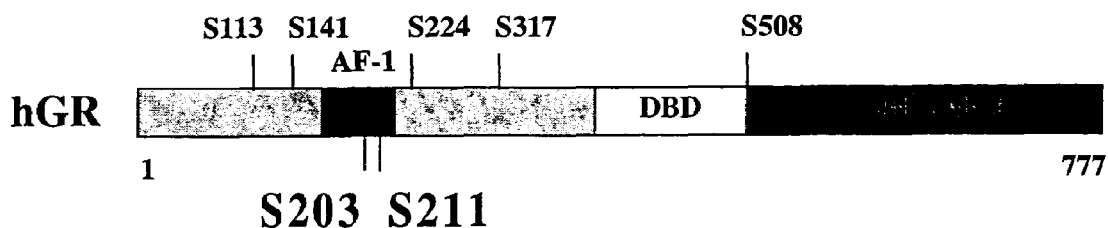

The glucocorticoid receptor (GR) is phosphorylated at multiple serine residues in a hormone-dependent manner. Yet, progress on elucidating the function of GR phosphorylation has been hindered by the lack of a simple assay to detect receptor phosphorylation in vivo. The present inventors have produced antibodies that specifically recognize phosphorylation sites within human GR at serines 203, 211 and 226 (S203, S211, and S226). In the absence of hormone, the level of GR phosphorylation at S211 and at S226 is low compared to phosphorylation at S203. Phosphorylation of all three residues increased upon treatment with the GR agonist dexamethasone. Using a battery of agonists and antagonists, the present inventors discovered that the transcriptional activity of GR correlates with the amount of phosphorylation at S211, suggesting S211 phosphorylation is a biomarker for activated GR in vivo. It appears from the initial results with S226 (FIGS. 2B and 2C) that S226 is similar to S211 and can serve as a biomarker for activated GR in vivo. Mechanistically, the kinetics of S203 and S211 phosphorylation in response to hormone differ, with S211 displaying a more robust and sustained phosphorylation relative to S203. Analysis of GR immunoprecipitates with the GR phospho-antibodies indicates that the receptor is phosphorylated heterogeneously on S203 in the absence of hormone, whereas in the presence of hormone, a subpopulation of receptors is phosphorylated on both S203 and S211. Interestingly, biochemical fractionation studies following hormone treatment indicate that the S203-phosphorylated form of the receptor is predominantly cytoplasmic, whereas the GR-S211phospho-form is found in the nucleus. Likewise, by immunofluorescence, the S203-phosphorylated GR is located in the cytoplasm and perinuclear regions of the cell, but not in the nucleoplasm, whereas strong phospho-S211 staining was evident in the nucleoplasm of hormone-treated cells. These results, which are presented in the Example herein below suggest that differentially phosphorylated receptor species are located in unique subcellular compartments, which likely modulates distinct aspects of receptor function.

The glucocorticoid receptor (GR) is a ligand-regulated transcription factor that controls diverse physiological and developmental processes by modulating gene expression. In addition, GR is an important therapeutic target for cancer and inflammatory diseases by "switching on" genes that stop cancer growth and "switching off" genes that cause inflammation. However, the ability to monitor the activated, hormone-bound GR in patients undergoing glucocorticoid therapy cannot be determined. GR is also a phospho-protein where GR phosphorylation occurs upon glucocorticoid binding. Thus, glucocorticoid hormone-dependent phosphorylation is a surrogate marker for activated GR in vivo.

The laboratory of the present inventors have produced antibodies that specifically recognize the phosphorylated form of human GR at serine residues 203, 211 and 226 (S203, S211 and S226) and found that the transcriptional activity of GR correlates with the amount of phosphorylation at S211 and S226, suggesting that S211 and S226 phosphorylation are important biomarkers for activated GR in vivo. This is the first time that phosphorylation site-specific antibodies have been produced against GR and the GR-P-S211 and GR-P-S226 antibodies represent regents for identifying whether GR is active or not in vivo. Thus, the present invention provides antibodies, and more generally, a molecule comprising the antigen binding portion of an antibody specific for glucocorticoid receptor phosphorylated at residue S203, at residue Ser211, or at residue Ser226.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')2 fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH–VL or single-chain FV). Both VH and VL may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be readily obtained by methods known to those skilled in the art. See, for example Kohler et al, (1975); U.S. Pat. No. 4,376,110; Harlow et al, (1988); and Colligan et al, (1994–2002), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al (1984), Morrison et al (1984), Boulianne et al (1984), European Patent 0 125 023 (1984), Neuberger et al (1985), European Patent 0 171 496 (1985), European Patent 0 173 494 (1986), WO 8601533 (1986), European Patent 0 184 187 (1986), Sahagan et al (1986); WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')2 fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

Glucocorticoids are used widely in clinical medicine, without any way of monitoring whether the GR is actually receiving the glucocorticoid signal and being activated. The molecules of the present invention, i.e., the phospho-GR antibody against the S211 or the S226 site, will allow monitoring of the response to glucocorticoid therapy by assaying GR phosphorylation at S211 or at S226 in target tissues or in serum.

Each year glucocorticoids are administered to more than 100,000 pregnant women that are at risk for giving birth to premature infants in order to facilitate fetal lung development. Clinical trials have demonstrated a substantial (>50%) reduction in morbidity and mortality in premature newborns whose mothers have received glucocorticoid therapy. However, a recent survey of obstetricians in the US reveals that a majority of practitioners repeat glucocorticoid administration weekly, and many continue to administer glucocorticoids to pregnant women with symptoms of preterm labor on an outpatient basis without monitoring response, despite provocative evidence that repeated administration of glucocorticoids decrease fetal neuronal growth and head size. Current tests in detecting changes in fetal lung maturation following glucocorticoid use are largely inadequate. Therefore, an assessment of glucocorticoid receptor activation using glucocorticoid receptor phosphorylation state-specific antibodies, in fetal cells obtained though amniocentesis, would represent a timely and accurate clinical test for the management of glucocorticoid therapy. GR phosphorylation state-specific antibody or the molecule according to the present invention can be used to monitor response to glucocorticoid therapy, since too much glucocorticoid activity has detrimental effects on both mother and fetus. In addition, these antibodies/molecules are also useful in predicting risk for preterm delivery or placental abnormalities, such as intrauterine growth restriction, caused by excessive glucocorticoid.

Non-limiting examples of other applications where response to glucocorticoid such as glucocorticoid resistance or dose response can be monitored include pulmonary disorders (i.e., asthma, emphysema), dermatologic disorders, rheumatologic disorders (autoimmunity), cancer therapy, and immune suppression in transplant surgery. For instance, patients receiving transplants are routinely given glucocorticoids to suppress their immune system so they do not reject the transplanted organ or tissue. However, a number of patients do not respond to glucocorticoid therapy. Lymphocytes from transplant patients can be monitored for GR activation using the phosphorylation site-specific antibodies/molecules of the present invention to determine which patients respond to glucocorticoid therapy. In dermatology, one use of glucocorticoids, besides treating disorders such as eczema, is to decrease wrinkle lines, and the GR phosphorylation-site specific antibodies/molecules can be used to monitor individual response and determine the optimal therapeutic window. In cancer therapy, most hematopoietic malignancies are generally treated with regimen of multiple chemotherapeutic agents in combination with steroids, although multiple myeloma is generally treated with steroid alone. As multiple myeloma is a disease of the bone marrow, obtaining tissue samples for assay would be relatively simple. A preferred target of therapy for most of the above-mentioned disorders and diseases is peripheral blood lymphocytes/neutrophils which can be readily sampled to monitor response or resistance to treatment with glucocorticoid. In terms of dose response, if glucocorticoid administration does not induce GR activation or induces too high an activation, as monitored by the phosphorylation site-specific antibody/molecule, then the dose of glucocorticoid can be adjusted accordingly.

The present invention provides a method for determining the presence of activated glucocorticoid receptors in cells obtained from human glucocorticoid responsive tissue using the GR phosphorylation-site specific antibody/molecule of the present invention. This method can be in vitro or in vivo and involves treating cells from glucocorticoid responsive human tissue of an individual with a glucocorticoid, reacting a sample of the treated cells or a cell extract thereof (such as is exemplified in the Example presented herein below) with the antibody/molecule of the present invention, and then detecting binding of the antibody/molecule to the treated cells or a cell extract thereof to determine the presence of activated glucocorticoid receptors in cells from glucocorticoid responsive human tissue of the individual.

When the glucocorticoid in the treating step is administered in vivo to an individual, then a sample of treated cells from glucocorticoid responsive human tissue of the same individual is removed from the individual before reacting the sample with the antibody or molecule of the present invention. Otherwise, the cells of glucocorticoid responsive human tissue of an individual can be treated in vitro with glucocorticoid.

While generally most tissues in humans are considered glucocorticoid responsive because they all have glucocorticoid receptors, there is variation in the degree of responsiveness. Examples of glucocorticoid responsive human tissue include thyroid, prostate, lung, and liver, which were used in experiments in the Example presented herein below. However, due to the ease of collecting samples, the source of cells of glucocorticoid responsive human tissue where phospho-GR can be measured is preferably blood, a buccal smear (scarping of the inside of the cheek), urine, amniotic fluid, or fluid from sites of inflammation (i.e., joints of arthritic patients). Other suitable sources of cells from glucocorticoid responsive human tissue can be readily ascertained by the degree of glucocorticoid responsiveness in general and the ease of obtaining a sample for assay.

The present invention further provides a method of screening for a glucocorticoid agonist, such as from a library of potential candidate. The method involves incubating human glucocorticoid responsive cells having glucocorticoid receptors in the presence or in the absence of a potential glucocorticoid agonist that activates glucocorticoid receptors and then reacting the incubated cells or cell extract thereof with the antibody or molecule of the present invention. Afterwards, the level of binding of the antibody or molecule of the present invention to the incubated cells or to a cell extract thereof is detected and based on the detected level of binding, identifying a potential glucocorticoid agonist as a glucocorticoid agonist if the level of activation of glucocorticoid responsive cells in the presence of the potential glucocorticoid agonist is substantially greater than in the absence of the potential glucocorticoid agonist. The term "substantially greater" or "substantially more" as used herein is intended to mean a level of activation in the presence of a potential glucocorticoid agonist at least about two times that of the basal level in the absence of this potential agonist. As the sensitivity of detection using the antibody or molecule of the present invention is quite good, even if the basal level of activation is very low, a two fold increase is detectable.

Having now generally described the invention, the same will be more readily understood through reference to the following example which is provided by way of illustration and is not intended to be limiting of the present invention.

EXAMPLE

To gain further insight into the function of GR phosphorylation in vivo, the laboratory of the present inventors has developed antibodies that specifically recognize human GR phosphorylated on either S203, S211 or S226. Using these novel reagents, the kinetics of hormone-dependent GR phosphorylation and the extent of receptor phosphorylation in response to a battery of agonists and antagonists as well as the subcellular localization of the phosphorylated GR in cultured cells and in human tissues were examined. The findings presented below in this example indicate that GR phosphorylation is a dynamic process, with differentially phosphorylated receptor species partitioned into distinct subcellular compartments which likely affect distinct aspects of receptor function in vivo.

EXPERIMENTAL PROCEDURES

Antibody Production

Phosphopeptides were synthesized by Anaspec Inc. (San Jose, Calif.) that correspond to the following sequences in human GR (GenBank accession no. PO4150): $_{194}$LQDLEFSSGS$^{PO4}$PGKE$_{207}$ (SEQ ID NO:1), $_{202}$GSPGKETNES$^{PO4}$PWRS$_{215}$ (SEQ ID NO:2), and $_{218}$LLIDENLLS$^{PO4}$PLAG$_{230}$. A cysteine residue was added to the N-terminus of each peptide to facilitate chemical cross-linking. Each phosphopeptide was coupled to KLH and used to immunize rabbits (Covance Research Products, Inc., Denver, Pa.). Sera from immunized rabbits were tested for antibody titer and specificity for the phosphorylated peptides by ELISA. High titer antibodies were further tested on human GR or rat GR expressed in U2OS or SAOS2 cells by immunoblotting.

Cell Culture and Preparation of Cell Extracts

The human lung carcinoma cell line A549 (CCL-185) containing endogenous GR and the human osteosarcoma cell line U2OS (HTB 96) lacking endogenous GR were obtained from the American Type Culture Collection and were cultured in Dulbecco's modified Eagle medium (DMEM; Cellgro), supplemented with either 5% or 10% fetal bovine serum (FBS; HyClone Laboratories, Inc., Logan, Utah), receptively, 2 mM L-glutamine, 50 µg/ml penicillin and 50 µg/ml streptomycin (Cellgro). Generation of stable U2OS cell lines ectopically expressing human GR (wild type and phosphorylation site mutants, S203A and S211A) was performed as previously described (Rogatsky et al., 1997). Cells were seeded at a density between 7 to $9 \times 10^5$ cells per 10 cm dish, 18 h prior to transfection. Cells were transfected using the calcium phosphate method with 10 to 15 µg of wild type pCMV$_{Neo}$-HA-hGR or phosphorylation site mutants pCMV$^{Neo}$-HA-hGR$_{S203A}$, PCMV$^{Neo}$-HA-hGR$_{S211A}$. Stable transformants were selected by culturing transfected cells in the presence of 800 µg/ml Geneticin (G418; Invitrogen, Carlsbad, Calif.) for 4–6 weeks. Individual neomycin-resistant clones were isolated and assayed for hGR expression by indirect immunofluorescence and immunoblotting with HA- and GR-specific antibodies. Clones homogeneously expressing HA-hGR were maintained at 500 µg/ml Geneticin.

Extracts for immunoblotting were prepared from a subconfluent 10 cm plate of A549 and U2OS-hGR cells treated with 100 nM dexamethasone (Dex) or equal volume of the ethanol vehicle 1 h prior to lysis. Cells were placed on ice, washed twice in phosphate-buffer saline (PBS), lysed in 0.5 ml of buffer containing 50 mM HEPES, pH 7.5, 150 mM NaCl, 1 mM EDTA, 1 mM EGTA, 1 mM NaF, 1% Triton X-100, 10% glycerol and additional protease and phosphatase inhibitors: 1 mM PMSF, 20 mM β-glycerophosphate, 8 mM sodium pyrophosphate, 1 µg/ml leupeptin, pepstatin A and aprotinin (Roche). Lysates were centrifuged at 12,000 rpm for 15 min at 4° C. The soluble supernatants were normalized for total protein concentration using the Bio-Rad protein assay (Bio-Rad Laboratories, Hercules, Calif.) and the samples were boiled for 3 min in 2×SDS sample buffer and stored at −20° C. Total lysates from human tissues were prepared from whole-tissue homogenates as described by the manufacturer (Protein Medleys; Clontech, Palo Alto, Calif.).

Immunoblotting

Cell extracts or immunoprecipitates containing GR were separated by 10% SDS-polyacrylamide gel electrophoresis (PAGE) and were transferred to Immobilon paper (Millipore Corp., Bedford, Mass.) at 110V for 80 min in Tris-Glycine transfer buffer. The membranes were blocked overnight in 5% bovine serum albumin (BSA) in Tris-buffered saline, pH 7.4 (TBS) (blocking solution) at 4° C., then were incubated in the blocking buffer with primary antibody at room temperature (RT) for 2–4 h using 1:1,000 and 1:10,000 dilution of serum for phospho-S211 (Ab353) and phospho-S203 (Ab211), respectively. Affinity purified phospho-S203 and phospho-S211 antibodies were also tested and results identical to that of the diluted sera were obtained. Endogenous GR was detected using the N499 polyclonal antibody, raised against residues 1–499 of the human GR. The membranes were washed three times for 10 min in TBS/0.1% Triton X-100 and twice in TBS and incubated for 1 h at RT with 0.2 μg/ml protein A conjugated to horseradish peroxidase (HRP) (Kirkegaard and Perry Laboratories, Gaithersburg, Md.). For blots using the anti-HA-tag monoclonal antibody (α-HA; Roche), an HRP-conjugated goat-anti-mouse IgG secondary antibody was used. Blots were then washed three times for 10 min in TBS-0.1% Triton X-100, twice in TBS and developed using enhanced chemiluminescence (ECL) according to manufacturer's instructions (Amersham Pharmacia Biotech Inc., Piscataway, N.J.). Quantitative analysis of immunoblots was performed using the NIH image software package (version 1.62).

Immunoprecipitation

For immunoprecipitation, the GR phosphorylation site-specific antibodies phospho-S203 and phospho-S211 and α-HA were prebound to protein A/G Plus agarose beads (Santa Cruz Biotechnology) in PBS at 4° C. for 1.5 hour and washed with PBS twice to remove the unbound antibody. Antibody-coated beads were incubated with 1 mg total protein of U2OS-hGR cell extract at 4° C. on a rotator for 3–5 h or overnight. Beads were washed 5 times in PBS and twice in 50 mM Tris pH 7.5 before boiling in 2×SDS sample buffer and stored at −20° C.

Immunofluorescence

U2OS-hGR cells were cultured in phenol red-free DMEM containing 10% charcoal-stripped FBS on coverslips coated with poly-D-Lysine and were treated with or without Dex for 1 h. Cells were fixed in cold acetone (−20° C.) for 15 min, air-dried and incubated in PBS containing 2.5% BSA for 1 h to block nonspecific protein binding. Cells were incubated with primary antibodies in blocking solution for 1 h RT, washed 5 times in PBS-0.1% Triton X-100, followed by incubation with goat anti-mouse or goat anti-rabbit fluorescein-conjugated secondary antibody (Vector Labs, Burlingame, Calif.) diluted in PBS, for 1 h at RT. Secondary antibody was removed by washing the cells five times in PBS-0.1% Triton X-100 and three times in PBS. Cover slips were mounted onto Citifluor (Ted Pella, Redding, Calif.), and the fluorescein signal was visualized and photographed using a Zeiss Axioplan 2 microscope.

Immunohistochemistry

An indirect immunoperoxidase method was used to identify phospho-S211 in normal human tissues arrays prepared by Dr. Herman Yee of NYU School of Medicine, Kaplan Comprehensive Cancer Center Molecular Diagnostics Shared Resource. Tissues were fixed for 2 h in PBS-4% paraformaldehyde at RT, dehydrated through ethanol, cleared in chloroform, and embedded in paraffin. Five-μm tissue sections were serially cut on a microtome and mounted on slides. Sections were dewaxed in xylene, rehydrated, and washed in TBS, pH 7.4. For antigen retrieval, paraffin sections were heated in a microwave oven for 15 min (900 watt, high power) in Target Retrieval Solution (DAKO, Carpinteria, Calif.), cooled and treated with 3% $H_2O_2$ for 15 min, rinsed with $H_2O$ and blocked with 20% normal goat serum for 30 min. Sections were incubated with phospho-S211 antibody (1:1,000 dilution) in 10% normal goat serum, washed, and a rabbit secondary biotinylated antibody was added, avidin-biotin complex formed, and developed using diaminobenzidine substrate. Slides were counterstained with hemotaxylin.

Preparation of Cytosolic and Nuclear Extracts

Nuclear extracts were prepared as described previously (Lee et al., 1998). U2OS-hGR cells (a single subconfluent 10 cm dish) were washed twice with cold PBS scraped into a 15 ml conical tube and pelleted by centrifugation at 1,200 rpm for 5 min at 4° C. An equal pellet volume (typically 100 μl) of buffer A (10 mM HEPES, pH 7.6, 1.5 mM $MgCl_2$, 10 mM KCl, 1 mM DTT, 0.2 mM sodium metabisulfite, 0.2 mM PMSF and a protease inhibitor cocktail was added, and the cells were allowed to swell on ice for 15 min. Cells were lysed by pushing them rapidly through a 1 ml hypodermic syringe with 25G ⅜" needle at least 5 times. The degree of cell lysis was monitored by light microscopy. The cell homogenate was centrifuged for 20 sec in a microcentrifuge at 12,000 rpm at 4° C. The supernatant was collected and saved as the cytosolic fraction. The nuclear pellet was resuspended in two thirds of cell pellet volume of buffer C (20 mM HEPES, pH 7.6, 25% glycerol, 420 mM NaCl, 1.5 mM $MgCl_2$, 0.2 mM EDTA, 1 mM DTT, 0.2 mM PMSF, 0.2 mM sodium metabisulfate and protease inhibitors) and incubated on ice with stirring for 30 min. The nuclear debris was pelleted by centrifugation for 5 min at 14,000 rpm and the supernatant collected as the nuclear fraction. Each sample was adjusted to equal protein concentration with buffer A or C, and an equal volume of 2×SDS sample buffer was added, boiled for 3 min and stored at −20° C.

Results

Characterization of hGR Phosphorylation Site Specific Antibodies

The polyclonal antibodies described in this study, GR phospho-S203, phospho-S211, and phospho-S226, were raised against the phosphopeptides LQDLEFSSGS$^{PO4}$PGKE (SEQ ID NO:1), GSPGKETNES$^{PO4}$PWRS (SEQ ID NO:2), and LLIDENLLS$^{PO4}$PLAG (SEQ ID NO:3) corresponding to residues 194 207, 202–215, and 218–230 of the human GR (FIGS. 1B and 1C), respectively.

Figure 2A:
FIGS. 2A–2C are immunoblots of hGR with phospho-S203 phospho-S211, and phospho-S226 antibodies.
Figure 2B:
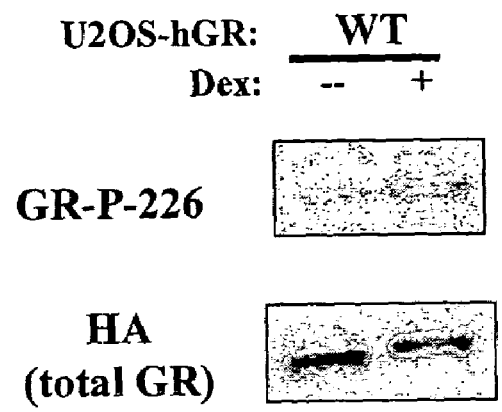
Figure 2C:
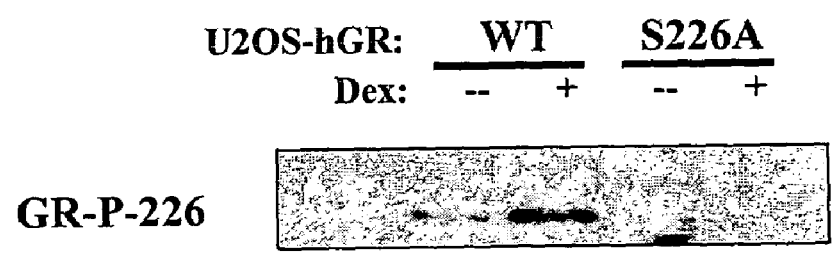

The antibodies were tested for their ability to detect GR by immunoblotting of extracts from U2OS cells ectopically expressing an HA-tagged version of human GR (U2OS-hGR) either untreated or treated for 1 h with dexamethasone (Dex). The phospho-S203 antibody recognized GR from both untreated and hormone-treated cells and showed somewhat greater immunoreactivity toward GR from cells stimulated with Dex (FIG. 2A, top panel, lanes 1 and 2). The phospho-S211 antibody showed substantial immunoreactivity toward GR from Dex-treated, rather than from untreated cells (FIG. 2A, center panel, lanes 1 and 2), even though equal amounts of GR were present as determined by immunoblotting for total GR using HA-epitope residing on the receptor (FIG. 2A, bottom panel, lanes 1 and 2). No immunoreactivity toward GR is observed with preimmune sera (not shown). These results indicate that S203 is phosphorylated in the absence and somewhat stronger in the presence of hormone, whereas S211 is phosphorylated predominantly in the presence of hormone.

As a control for specificity, the ability of the antibodies to detect phosphorylation-deficient forms of GR S203A and S211A in U2OS cells (U2OS-hGR$_{S203A}$ and U2OShGR$_{S211A}$) was tested. The phospho-S203 antibody did not recognize GR S203A in either the absence or presence of Dex (FIG. 2A, top panel, lanes 3 and 4), but still recognized the phosphorylation-deficient GR derivative S211A (FIG. 2A, top panel, lanes 5 and 6), to similar extent as wild type GR. The same relationship holds for the phospho-S211 antibody: it did not detect the hGR S211A mutant (FIG. 2A, center panel, lanes 5 and 6), but was reactive with the S203A derivative in a hormone-dependent manner (FIG. 2A, center panel, lanes 3 and 4), albeit to a slightly lesser extent than with wild type GR (FIG. 2A, center panel, compare lanes 2 and 4). The finding that the S203A mutation reduces phosphorylation at the S211 site suggests an interdependency of these two sites on each other, such that S203 may need to be phosphorylated first, before efficient phosphorylation of S211 can occur. Total amount of GR in each lane was equivalent as revealed by immunoblotting with the HA antibody (FIG. 2A, bottom panel). Thus, each antibody recognized its cognate GR phosphorylation site specifically.

Endogenous hGR Phosphorylation in Human Cells and Tissues

GR phosphorylation in the human lung carcinoma cell line A549 that expresses endogenous GR was next examined. As observed in U2OS cells ectopically expressing hGR, the level of endogenous hGR phosphorylation in A549 cells at S211 is low compared to phosphorylation at S203 in the absence of hormone. Phosphorylation of both residues increased upon treatment with the agonist dexamethasone (FIG. 3). Thus, the phospho-S203 and phospho-S211 antibodies are capable of detecting phosphorylation of endogenous GR from a cultured cell line.

Human GR phosphorylation from lysates of human tissues was also investigated by immunoblotting (FIG. 4). Of the four GR responsive tissues examined, thyroid, prostate, lung and liver, abundant GR phospho-S203 and phospho-S211 reactivity was observed in the prostate and liver, whereas weak phospho-GR immunoreactivity was observed in the thyroid. The same pattern holds true for total GR. We were unable to detect phospho-GR in the lung sample, even upon prolonged exposure (not shown), although a small amount of total GR was observed. Thus, prostate, thyroid and liver from normal human tissues contain phospho-GR isoforms.

To determine which cell types display the S211-phosphorylated form of GR, serial sections of normal human tissues were examined by immunohistochemistry with either the GR phospho-S211 antiserum or an antibody that recognizes GR independent of its phosphorylation state (total GR) (FIGS. 5A–5H). A section of a human lymph node shows strong phospho-S211 immunoreactivity within the nuclei of lymphocytes, a pattern reflected in the staining for total GR. Similarly, the nuclei of thyroid cells react with the phospho-S211 antibody, whereas both the cytoplasm and nuclei of islet cells of the pancreas stain positive. In contrast, lung tissue shows little phospho-S211 immunoreactivity within the alveolar cells, despite immunoreactivity of their cytoplasm to total GR antibody. This low level of immunoreactivity is consistent with the results from the immunoblotting analysis of lung extracts (FIG. 4). Although alveolar cells showed no detectable phospho-S211 immunoreactivity, macrophages resident in the lung appear to contain phospho-S211 GR, indicating that the staining procedure worked. Thus, the S211-phosphorylated, hormone-activated form of GR is readily detected in vivo in a subset of normal human tissues.

Effects of Agonists and Antagonists on hGR Phosphorylation of S203 and S211

Figure 6A:
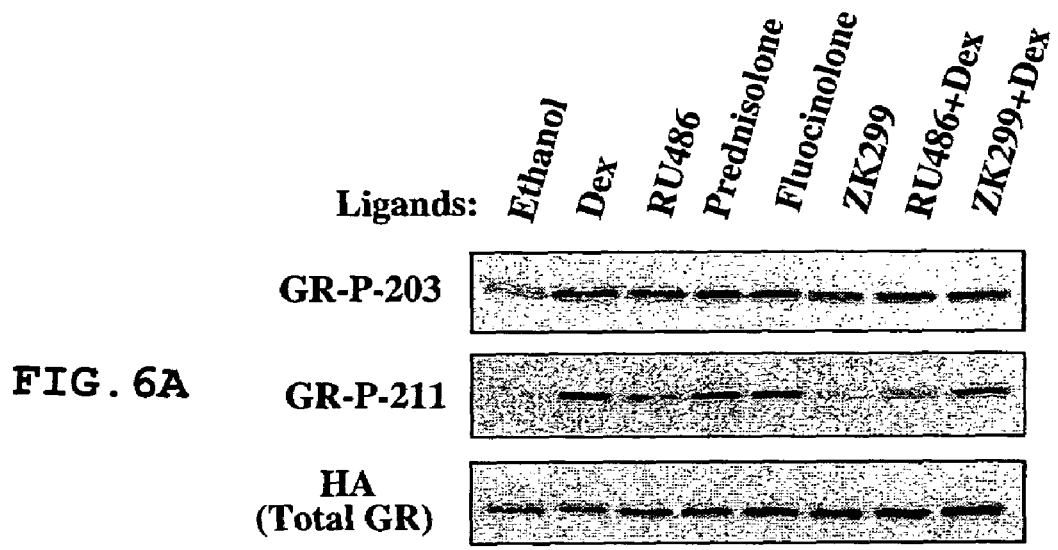
FIGS. 6A and 6B show the effects of agonists and antagonists on GR phosphorylation and transcriptional activation.
Figure 6B:
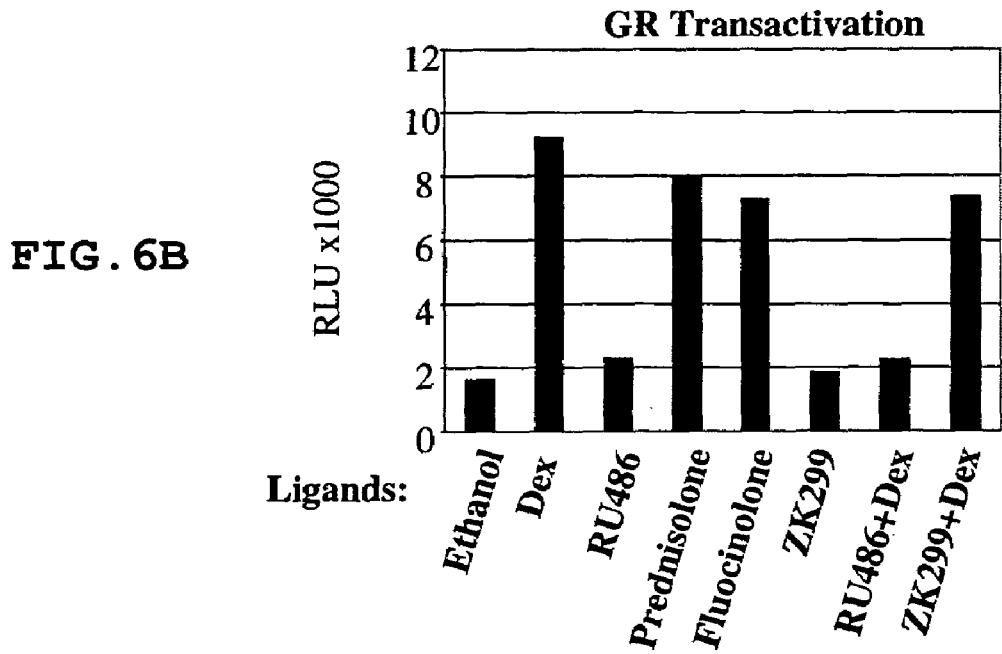

The influence of different glucocorticoid agonists and antagonists on phosphorylation of GR was also examined. Three kinds of glucocorticoid agonists, Dex, Prednisolone and Fluocinolone, and two types of glucocorticoid antagonists, RU486 and ZK299 were tested for their ability to induce GR phosphorylation and affect GR-mediated transcriptional activation after 1 hour of treatment. As shown in FIGS. 6A and 6B, Dex, Prednisolone and Fluocinolone promoted S211 phosphorylation, whereas RU486 only minimally stimulated phosphate addition to S211, a pattern mirrored in the GR transcriptional activation assay. For the S203, Dex and RU486 induced roughly the same amount receptor phosphorylation (FIG. 6A). ZK299 had almost no effect on the phosphorylation of either S203 or S211. In addition, a 10-fold molar excess of RU486 over Dex could effectively block the Dex-dependent stimulation of S211 phosphorylation. A 10-fold excess of ZK299 was not as effective at blocking Dex-dependent phosphorylation of GR, presumably owing to its lower affinity for the receptor. These results suggest that the GR-mediated transcriptional activity correlates with GR phosphorylation, suggesting an association between receptor-dependent transcriptional enhancement and S211 phosphorylation.

Kinetics of S203 and S211 Phosphorylation in Response to Hormone

Figure 7A:
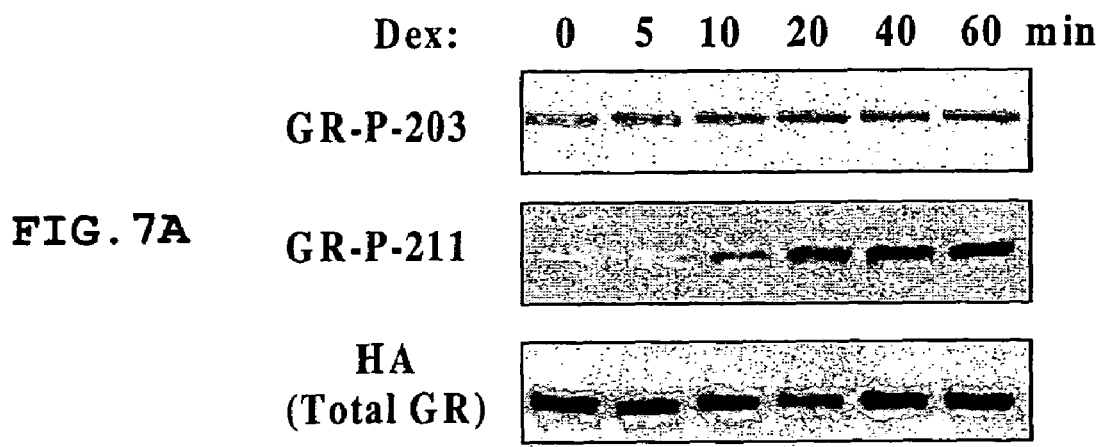
FIGS. 7A–7C are immunoblots and graph showing the kinetics of S203 and S211 phosphorylation in response to Dex treatment. U2OS-hGR cells were treated with ethanol (−) or Dex (100 nM) for the time indicated. Whole cell lysates were prepared, normalized and analyzed by immunoblotting with phospho-S203, phospho-S211 or HA antibodies. Immunoblot images of GR phosphorylated at S203 and S211 in the first hour of Dex treatment (FIG. 7A) or throughout 12 h of continuous Dex treatment (FIG. 7B); the total GR in each sample was determined by immunoblotting for HA.
Figure 7B:
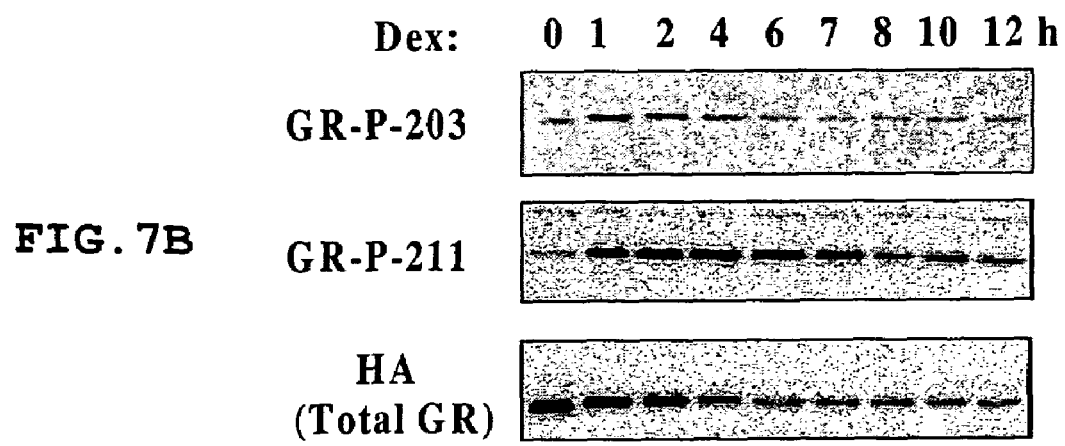
Figure 7C:
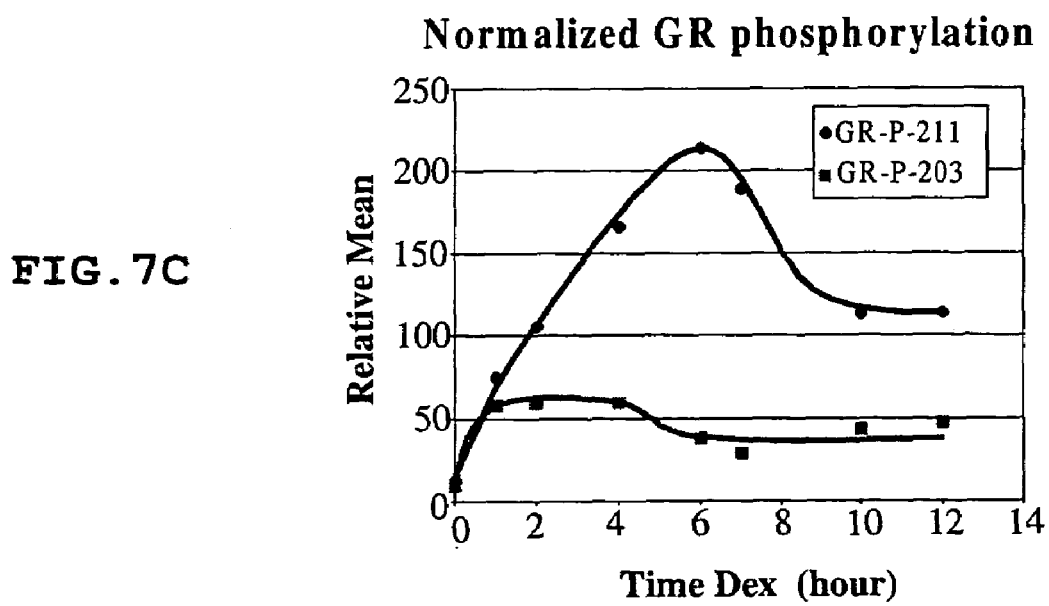

To examine the kinetics of phosphorylation of S203 and S211, immunoblots of U2OS-hGR extracts made at different times of Dex treatment using the phospho-S203 and phospho-S211 antibodies were performed (FIGS. 7A–7C). The HA antibody was used to determine the total amount of GR. The relative amount of immunoreactivity for each time point was quantitated. Hormone treatment had little effect on total GR at 1 h, but resulted in a time-dependent decrease in GR that started at 2 h of hormone treatment and continued for 12 h; such decrease in GR protein level has been previously attributed to increased GR mRNA and protein turnover (Burnstein et al., 1994 and Liu et al., 2000). Total GR was reduced by nearly 80% by 12 h of continuous hormone treatment. As shown in FIG. 7A, phosphorylation at S211 increased rapidly within the first hour of Dex treatment, reaching a plateau within 20 to 40 min of hormone treatment. On a longer time scale, S211 phosphorylation remained high for 6 h, after which the apparent signal decreased progressively from 7 to 12 h (FIG. 7B). Phosphorylation of S203 increased at a rate similar to that of S211 within the first hour of hormone treatment (FIG. 7B, top panel). When normalized to GR protein at each time point, S203 phosphorylation increased at 1 h of Dex treatment and remained almost unchanged relative to total GR between 1 and 12 h (FIG. 7C). This result indicates that S203 phosphorylation reaches a maximum at 1 h of Dex treatment and then parallels the kinetics of down regulation of GR. In contrast, S211 phosphorylation increased more markedly and at a slower rate than S203 phosphorylation, reaching a maximum at 6 h of hormone treatment and decreased at the same rate as total GR after 10 h (FIG. 7C). Thus, hormone-dependent phosphorylation at S211 is more robust and sustained than S203 phosphorylation.

Heterogeneity of GR Phosphorylation

Figure 8:
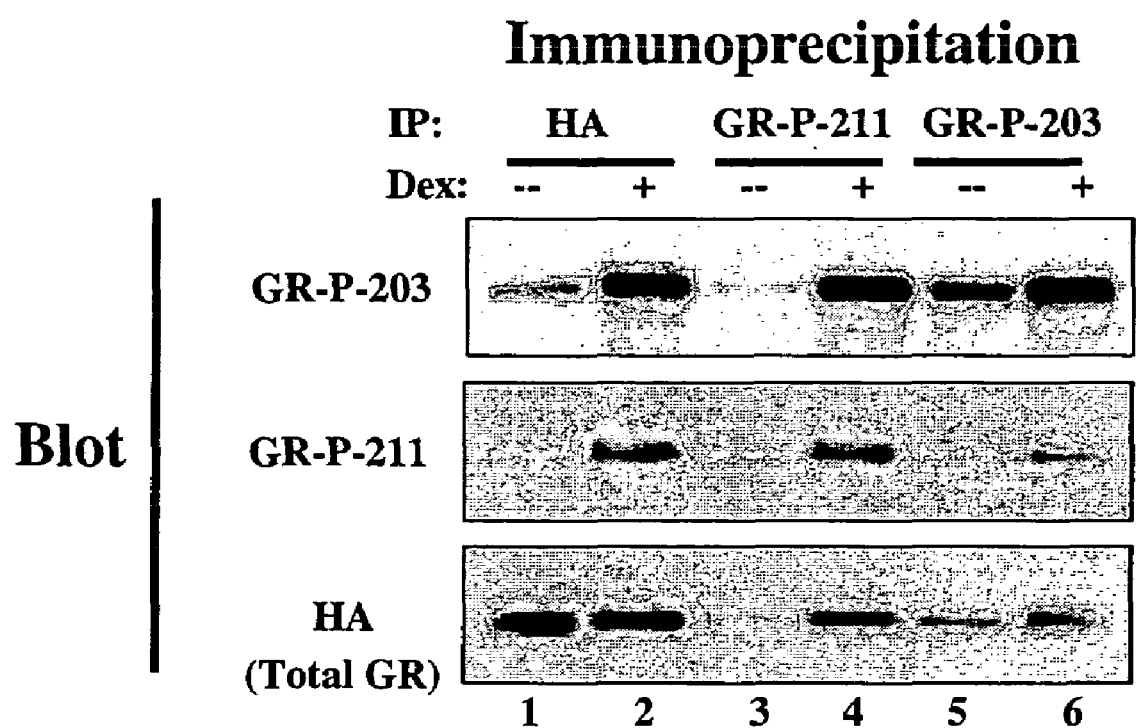
FIG. 8 are immunoblots showing phosphorylation of GR on both S203 and S211 in response to Dex treatment and heterogeneous phosphorylation of S203 in untreated cells. Immunoprecipitation of the phosphorylated forms of GR by phospho-S203 and phospho-S211 antibodies. U2OS-hGR cells were treated with either ethanol or 100 nM Dex for 1 h and whole cell extracts containing equal amounts of protein were immunoprecipitated with using either phospho-S203, phospho-S 211 or HA antibodies. Immunoprecipitates were analyzed by immunoblotting with phospho-S203, phospho-S211 and HA antibodies.

Results from the immunoblot analysis indicate that GR is phosphorylated at S203 and S211 in the presence of Dex. However, this finding does not distinguish between receptors with a single phosphate moiety at each site or receptor molecules that are phosphorylated at S203 and S211 simultaneously. To address this issue, GR was immunoprecipitated with phospho-S203, phospho-S211 or HA from lysates of U2OS-hGR cells that had been cultured with or without Dex for 1 h. The immunoprecipitates were analyzed by immunoblotting with HA and the GR phospho-specific antisera. As expected, the HA antibody immunoprecipitated an equivalent amount of GR from Dex-treated or untreated cells (FIG. 8; bottom panel, lanes 1 and 2). The phospho-S211 antiserum preferentially immunoprecipitated GR from Dex-treated cells (FIG. 8, lanes 3 and 4), whereas the phospho-S203 antibody immunoprecipitated GR from hormone-treated and untreated cells, with more GR being precipitated from the Dex-treated sample (FIG. 8, lanes 5 and 6). The immunoprecipitation results are consistent with the immunoblotting of whole cell extracts, and support the idea that phosphorylation at S211 is largely hormone-dependent, whereas phosphorylation of S203 occurs in the absence of hormone but is increased upon hormone stimulation. Importantly, the hGR S211 immunoprecipitate was recognized by the phospho-S203 antibody and visa versa, indicating that GR can be phosphorylated on S203 and S211 simultaneously (FIG. 8, top and center panels, lanes 3–6). Therefore, a population of GR molecules that is doubly phosphorylated on both S203 and S211 resides in vivo.

The fact that phosphorylation at S203 is increased in response to hormone suggest that not all GR is basally phosphorylated on S203. Indeed, if GR were homogeneously phosphorylated at S203, then the present inventors would anticipate that total GR and phospho-S203 immunoprecipitates would produce the same immunoreactivity when blotted with GR phospho-S203 antibody. In contrast, if GR were heterogeneously phosphorylated at S203, then the present inventors would expect to see less GR phospho-S203 immunoreactivity from immunoprecipitates of total GR versus phospho-S203, which is observed experimentally (FIG. 8, compare lanes 1 and 5; top panel). Therefore, within a population of GR molecules in the absence of hormone in vivo, some receptors are phosphorylated at S203, whereas others remain unphosphorylated.

The Subcellular Location of hGR Phospho-S203 and Phospho-S211 Isoforms

Figure 9:
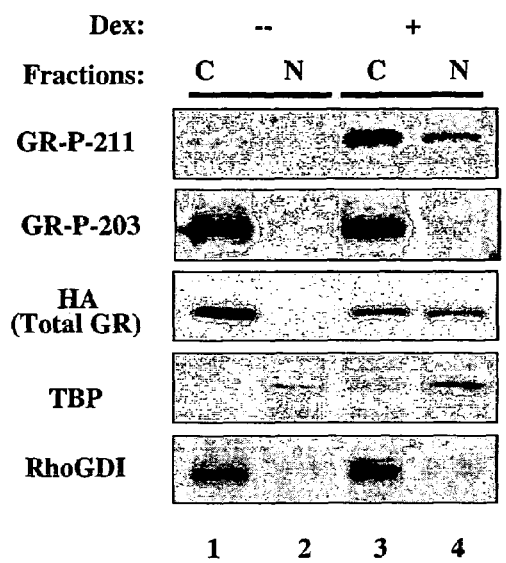
FIG. 9 are immunoblots showing the subcellular localization of phospho-S203 and phospho-S211 GR in U2OS-hGR cells. Cytosolic (C) and nuclear (N) extracts were prepared from U2OS-hGR cells treated with ethanol or 100 nM Dex for 1 h. Equal amounts of protein from each fraction were analyzed by immunoblotting with either phospho-S203, phospho-S211 or HA antibodies. Fractions were immunoblotted for cytosolic and nuclear marker proteins, RhoGDI$\alpha$ and TBP, respectively, to ensure the integrity of the fractionation procedure.

To determine the subcellular location of GR phosphorylation, cytosolic and nuclear fractions from U2OS-hGR cells either untreated or treated with Dex for 1 h were prepared. In the absence of hormone, GR was detected exclusively in the cytosol fraction, while after a 1 h Dex treatment the receptor was distributed equally between cytosol and the nuclear fractions (FIG. 9). Interestingly, phosphorylation of S203 in the absence and presence of Dex was detected exclusively in the cytosolic fraction of U2OS cells, whereas phosphorylation of S211 was observed in both the cytosolic and nuclear fractions (FIG. 9, lanes 1–4). To ensure the fidelity of the fractionation procedure, each fraction for the cytosolic and nuclear marker proteins, RhoGDIα, a Rho guanine nucleotide dissociation inhibitor, and TATA-box binding protein (TBP), a member of the $TF_{II}D$ transcriptional regulatory complex were examined. As expected, RhoGDIα was found predominantly in the cytosolic fraction, whereas TBP immunoreactivity was observed primarily in the nuclear fraction. Thus, the procedure accurately separated the cytoplasmic and nuclear fractions. These results suggest that S203 and S211 are phosphorylated in the cytoplasm and that the S211-phosphorylated form of the receptor resides in the nucleus after a 1 h hormone treatment.

Figure 10:
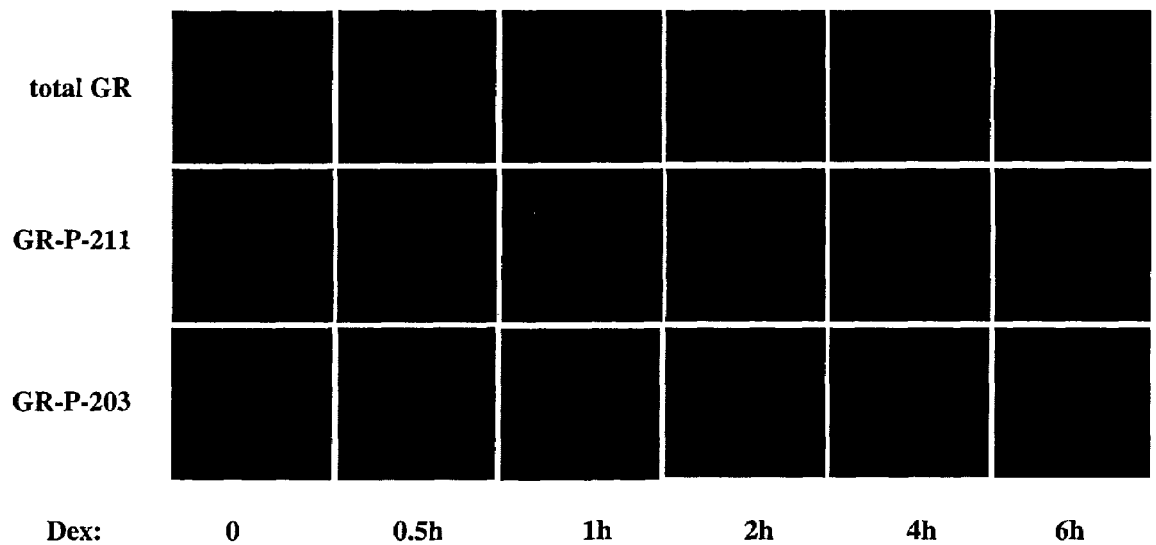
FIG. 10 are immunofluorescence studies in which U2OS-hGR cells are treated exactly as above in FIG. 9, with either ethanol (0) or 100 nM Dex for the times indicated and were fixed, and the subcellular location of GR was examined by indirect immunofluorescence using phospho-S203, phospho-S211 or HA antibodies as a measure of total GR. The data shown are from a single experiment that is representative of at least three independent experiments.

Immunofluorescence was performed with phospho-S203 and phospho-S211 antibodies and yielded results consistent with the fractionation studies (FIG. 10). In untreated U2OS-hGR cells, the S203-phosphorylated form of the receptor was observed primarily in the cytoplasm and perinuclear region of the cell, but not in the nucleoplasm. Upon hormone treatment, the same pattern holds true, with stronger perinuclear phospho-S203 immunoreactivity observed. Virtually no phospho-S211 immunoreactivity was observed in the cytoplasm or nucleus of untreated cells. In contrast, strong phospho-S211 staining was evident in the nucleoplasm of hormone-treated cells after a 1 h hormone treatment, with diffuse phospho-S211 immunoreactivity observed in the cytoplasm. This staining is specific to phospho-GR since no immunofluorescence was observed above background in U2OS-hGR$_{S203A}$ and U2OS-hGR$_{S211A}$ cells when examined with the phospho-S203 and phospho-S211 antisera, respectively (not shown). Together, these results suggest that the S203-phosphorylated form of GR is predominantly cytoplasmic and perinuclear, whereas the S211-phosphophorylated species is strikingly nuclear after hormone stimulation.

Figure 11:
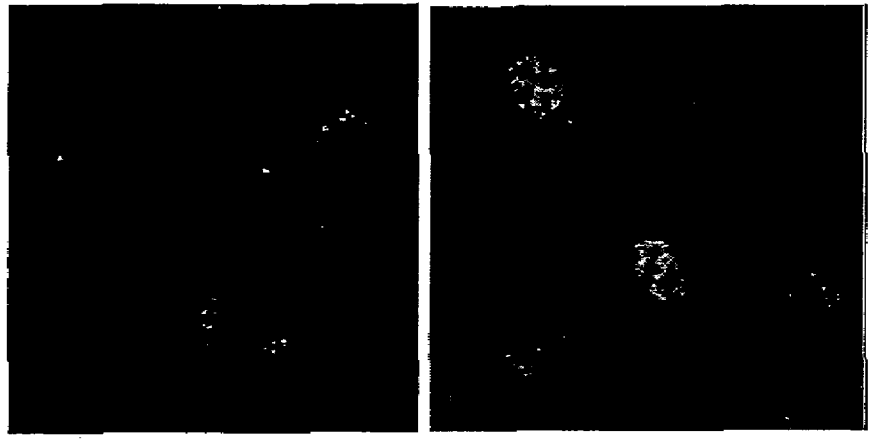
FIG. 11 show the subcellular distribution of endogenous phospho-S203 and phospho-S211 GR in A459 cells by indirect immunofluorescence. A549 cells, which contain endogenous GR, were treated with either ethanol (−) or 100 nM Dex (+) for 1 h, fixed, and the subcellular location of GR was examined by indirect immunofluorescence using the phospho-S203 and phospho-S211 antibodies or the phosphorylation state-independent antibody, GR N499 (total GR).
Figure 11:
Figure 11:
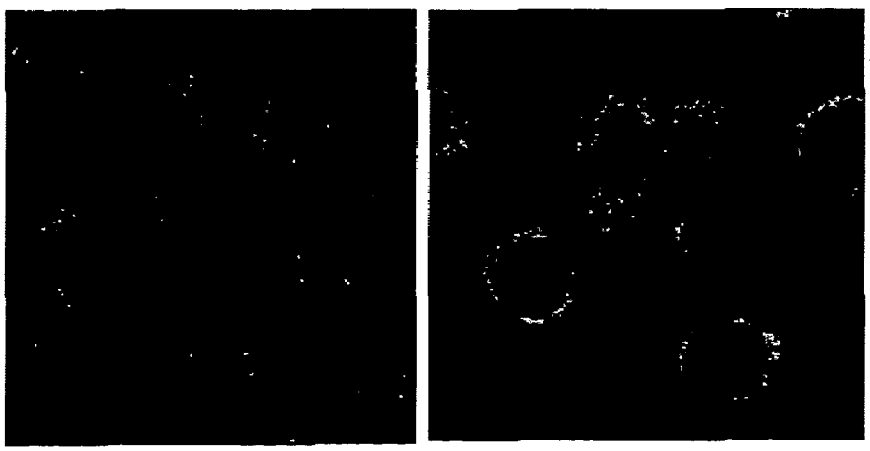

The subcellular distribution of the phospho-S203 and phospho-S211 hGR isoforms in A549 cells was also examined (FIG. 11). As was observed in U2OS-hGR cells, strong phospho-S211 immunoreactivity was observed in the nuclei of hormone treated cells, whereas the S203-phosphorylated form of the receptor was distributed primarily throughout the perinuclear region. These results corroborate the findings in U2OS-hGR cells and suggest that different phosphorylated isoforms of GR localize to distinct subcellular compartments.

Discussion

The laboratory of the present inventors has generated antibodies that specifically recognize hGR phosphorylated on S203 and S211. Both antibodies react with specific GR phosphorylation states by immunoblotting or immunoprecipitation, suggesting that the antibodies detect the phosphorylated receptor in either its native or denatured form (FIGS. 2 and 8). There appears to be a significant basal level of GR phosphorylation at S203 but not S211, and phosphorylation of both residues was increased upon treatment with Dex. This is consistent with results of $^{32}P$ metabolic labeling studies (Krstic et al., 1997 and Bodwell et al., 1993). The enhancement of phosphorylation at S203 is about 2-fold, whereas for S211 it is approximately 10-fold after a 1 h of Dex treatment (FIGS. 7A–7C).

A strong correlation between S211 phosphorylation of GR and receptor transactivation was also found; potent agonists, such as Dex and Prednisolone, induced robust GR phosphorylation at S211, while mixed agonists/antagonists, such as RU486, elicited only modest receptor phosphorylation (FIGS. 6A and 6B). Effect of RU486 on GR phosphorylation at S211, suggests that the kinase phosphorylating this residue may be recruited to the receptor via the ligand binding domain, with RU486 affecting this association. Recently, Chen, et al. demonstrated that AF-1 activity of the estrogen receptor alpha (ER) is modulated by phosphorylation as a result of the ligand-dependent recruitment of a Cdk through the receptor's ligand-binding domain (Chen et al., 2000). Whether GR phosphorylation of S211 operates through a similar mechanism remains to be tested.

Conceivably, phosphorylation of S211 may alter the receptor conformation or modulate interactions with cofactors that facilitate transactivation. Consistent with this latter notion, GR interaction with the AF-1 cofactor DRIP150 is reduced when S211 is mutated to alanine (A. Hittelman and M. Garabedian, unpublished observation). In addition, the phospho-S211 antibody was capable of recognizing GR within normal human tissues by immunohistochemistry. Thus, phosphorylation of S211 may represent an important biomarker for the hormone-activated form of GR in vivo.

The time course of S203 and S211 phosphorylation in response to continuous Dex treatment showed that S211 phosphorylation was more sustained than S203 phosphorylation, suggesting that phosphorylation at S203 is more labile than phosphorylation at S211. Whether phospho-S203 and phospho-S211 are differentially sensitive to the same phosphatase, represent targets for distinct phosphatase(s), or whether partitioning of S211 into the nucleus protects it from dephosphorylation or promotes hyperphosphorylation remains to be determined.

It is interesting to note that down-regulation of GR occurs at the same rate as S203 phosphorylation, suggesting that modification of this residue might be a determinant of ligand-dependent down-regulation of GR. This would be consistent with the finding of Webster et al. that characterized phosphorylation site mutations that stabilize the GR and decreased its ligand-dependent down-regulation (Webster et al., 1997).

Subcellular localization of the phospho-GR isoforms assessed biochemically indicate that upon hormone stimulation the S203 phosphorylated forms of the receptor is detected in the cytoplasm, whereas GR-P-211 is evident in both the cytoplasmic and nuclear fractions (FIG. 9). Interestingly, by immunofluorescence, the S203 phosphorylated form of the receptor is confined primarily to the cytoplasm and perinuclear regions of the cell, whereas the receptor phosphorylated at S211 localizes to the nucleoplasm and cytoplasm after a 1 h hormone stimulation (FIG. 10). These findings suggest that unique phosphorylated forms of the receptor are distributed to distinct subcellular compartments: the GR phospho-S211 form corresponds to the nuclear transcriptionally active subpopulation of the receptor, whereas the GR phospho-S203 form is perinuclear, possibly affiliated with receptor function(s) at the cytoplasmic/nuclear border, such as nuclear import or export. Alternatively, GR phosphorylation may represent a quality control step or checkpoint that insures that the receptor is properly configured for events such as cofactor binding. Thus, specific subpopulations of GR with different phosphorylation patterns may modulate distinct aspects of receptor function in vivo.

The first phosphorylation state-specific antibodies against a steroid receptor, the progesterone receptor (PR), were described in an elegant set of experiments by Clemm et al. (Clemm et al., 2000). As with GR, the PR hormone-dependent phosphorylation sites are regulated differentially over time. However, unlike GR, PR phosphorylated forms examined appear to reside in the nucleus. Whether this reflects differences in the phosphorylation sites examined between GR and PR, or receptor kinases and phosphatases that target these receptors will require further study.

Figure 12:
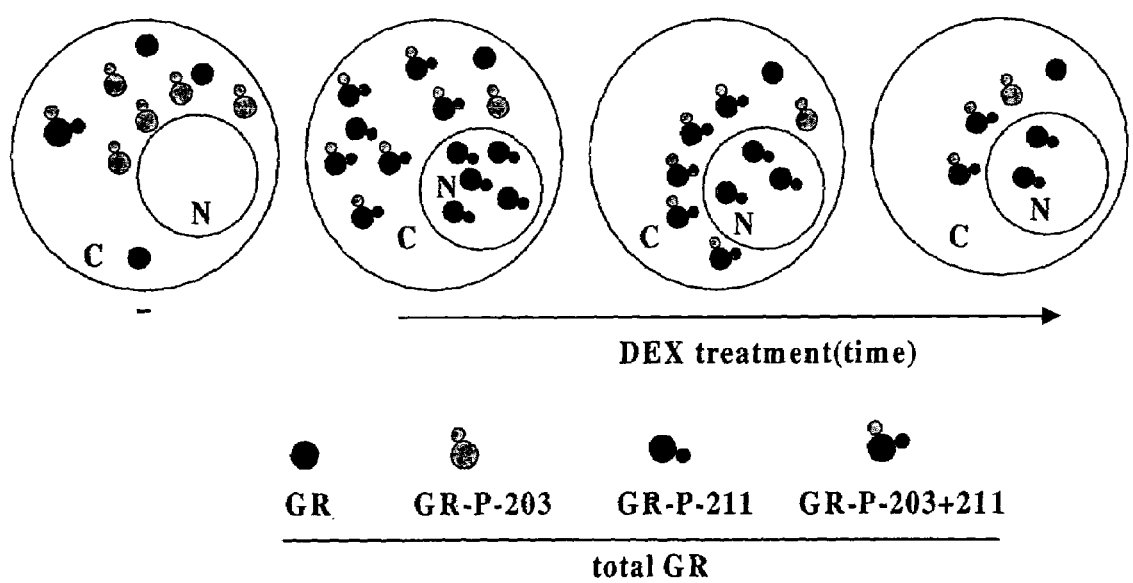
FIG. 12 shows a model for GR-dependent phosphorylation. In the absence of hormone, the phosphorylated subpopulation of GR is mostly modified on S203 (light large+small circles), a population of unphosphorylated receptor molecules may also be present (dark circle); hormone treatment promotes phosphorylation of both S203 and S211 (dark large+small circles), causing an increase in doubly phosphorylated form GR-P-S203–S211 (dark large+small circles and small light circle). As time progresses, GR-P-S203 undergoes dephosphorylation such that the ratio of GR phosphorylated on S211 to those phosphorylated on S203 increases. Differential modification of GR by phosphorylation induces a distinct conformation and/or influences the receptor association with additional coregulatory proteins that modulate GR transactivation, stability and subcellular location.

Based on the results presented in this example, the present inventors propose a model of GR modulation by phosphorylation, whereby in the absence of hormone, the phosphorylated subpopulation of GR is mostly modified on S203; hormone treatment promotes phosphorylation of both S203 and S211, causing an increase in doubly phosphorylated form GR-P-S203/S211 (FIG. 12). The present inventors speculate that this doubly phosphorylated version of GR "primes" the receptor for S203-P dephosphorylation, resulting in the mono-S211 phosphorylated version of the receptor that accumulates in the nucleus. This mechanism is analogous to substrate "priming" by kinases, such as glycogen synthase kinase-3, where a prior phosphorylation event generates the substrate for subsequent modification (Dajani et al., 2001). As time progresses, GR-P-S 211 phosphorylation and GR-P-S203 dephosphorylation continues increasing the ratio of GR-P-S211 to GR-P-S203. The S211-phosphorylated form enters the nucleus where phosphorylation remains high, however, exit from the nucleus leads to S211 dephosphorylation, resulting in a "naked" receptor subspecies that lacks a phosphate adduct on either S203 or S211. The receptor can then adopt two fates: it can either be recycled or degraded. "Naked" receptors may reassemble into chaperone-bound aporeceptor complexes, which would facilitate S203 phosphorylation, thus re-establishing the GR-P-S203 form. Receptors that do not associate with the hsp90 chaperone complex are subject to degradation. This notion is consistent with the previous studies, whereby treatment of cells with the hsp90 inhibitor geldanamycin promoted GR degradation by the proteosome (Segnitz et al., 1997). Although further experiments will be necessary to distinguish whether phosphorylation promotes receptor recycling or degradation, this cycle of phosphorylation and dephosphorylation likely plays a key role in modulating the hormonal response in vivo.

Protein phosphatases types 1, 2A and 5 (PP1, PP2A, and PP5) have been shown to associate with GR and affect receptor function and phosphorylation (DeFranco et al., 1991; Silverstein et al., 1997 and Zuo et al., 1999). Inhibition of phosphatase activity by okadaic acid results in GR hyperphosphorylation, a redistribution of the receptor from the nucleus to the cytoplasm, and the inability of GR to re-enter the nucleus (Somers et al., 1992). The present inventors speculate that inhibition of the phosphatase activity leads to an accumulation of the doubly phosphorylated form GR-P-S203/S211 in the cytosol by virtue of decreased entry into or increased exit from the nucleus.

The findings here also shed light on the kinases that target the GR. Biochemical fractionation studies suggest that GR phosphorylation at both S203 and S211 occurs in the cytoplasm, with the S211-phosphorylated form accumulating the nucleus. Previous results from the laboratory of the present inventors have shown that cyclin E/Cdk2 and cyclin A/Cdk2 phosphorylate GR at S203 and that cyclin A/Cdk2 targets S211 in vitro (Krstic et al., 1997). Since the active forms of these kinases are predominantly nuclear (Maridor et al., 1993), it is unlikely that these represent the receptor kinases that promote phosphorylation at S203 and S211 in the cytoplasm. However, it is conceivable that two distinct kinases, one cytoplasmic and the other nuclear, target S211 and that cyclin A/Cdk2 is the receptor kinase that promotes S211 phosphorylation in the nucleus. In light of the dual phosphorylation of ERa S118 by Erk and Cdk (Chen et al., 2000 and Bunone et al., 1996), it is possible that GR may be similarly targeted by multiple kinases depending upon the subcellular compartment the receptor occupies.

The present inventors suggest that differential modification of GR by phosphorylation induces distinct conformations and/or influences the receptor association with additional coregulatory proteins that modulate GR transactivation and stability. Phosphorylation of GR represents a unique modification "code" that is deciphered in the nucleus and cytoplasm to differentially affect receptor function. Subsets of phosphorylated receptor species with distinct functions may emerge as a novel and general mechanism governing steroid hormone receptor action.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated molecule comprising the antigen binding portion of an antibody specific for human glucocorticoid receptor phosphorylated at residue Ser 211 or at residue Ser 226 of SEQ ID NO: 4.

2. The molecule of claim 1, which is a polyclonal antibody.

3. The molecule of claim 1, which is a monoclonal antibody.

4. The molecule of claim 1, which is specific for the sequence of SEQ ID NO:2.

5. The molecule of claim 1, which is specific for the sequence of SEQ ID NO:3.

6. A method for determining the presence of activated glucocorticoid receptors in cells obtained from human glucocorticoid responsive tissue, comprising:
  treating cells from glucocorticoid responsive human tissue of an individual with a glucocorticoid;
  reacting a sample of the treated cells or a cell extract thereof with the molecule of claim 1;
  detecting binding of the molecule of claim 1 to the treated cells or a cell extract thereof to determine the presence of activated glucocorticoid receptors in cells from glucocorticoid responsive human tissue of the individual.

7. The method of claim 6, wherein said treating step comprises administering a glucocorticoid to an individual in need thereof and wherein a sample of treated cells from glucocorticoid responsive human tissue of an individual is removed from the individual before said reacting step.

8. A method of screening for a glucocorticoid agonist, comprising:
  incubating human glucocorticoid responsive cells having glucocorticoid receptors in the presence or absence of a potential glucocorticoid agonist that activates glucocorticoid receptors;
  reacting the incubated cells or cell extract thereof with the molecule of claim 1;
  detecting the level of binding of the molecule of claim 1 to the incubated cells or cell extract thereof;
  determining from the detected level of binding the level of activation of glucocorticoid responsive cells to the potential glucocorticoid agonist in the presence of the potential glucocorticoid agonist relative to the level of activation in the absence of the potential glucocorticoid agonist; and
  identifying as a glucocorticoid agonist for which said determining step determines that the level of activation of glucocorticoid responsive cells in the presence of the potential glucocorticoid agonist is substantially more than that in the absence of the potential glucocorticoid agonist.

9. An isolated molecule comprising the antigen binding portion of an antibody specific for human glucocorticoid receptor phosphorylated at residue Ser 203 of SEQ ID NO: 4.

10. The molecule of claim 9, which is a polyclonal antibody.

11. The molecule of claim 9, which is a monoclonal antibody.

12. The molecule of claim 9, which is specific for the sequence of SEQ ID NO:1.

* * * * *